United States Patent [19]

Richter et al.

[11] 4,217,436

[45] Aug. 12, 1980

[54] POLYURETHANE FORMING COMPOSITIONS

[75] Inventors: Reinhard H. Richter, North Haven; Benjamin W. Tucker, Bethany; Henri Ulrich, Northford, all of Conn.

[73] Assignee: The Upjohn Company, Kalamazoo, Mich.

[21] Appl. No.: 968,251

[22] Filed: Dec. 11, 1978

Related U.S. Application Data

[60] Division of Ser. No. 874,402, Feb. 1, 1978, Pat. No. 4,138,398, which is a continuation-in-part of Ser. No. 754,189, Dec. 27, 1976, abandoned.

[51] Int. Cl.² .................. C08G 18/80; C08G 18/77; C07D 243/04; C07D 245/02
[52] U.S. Cl. .................. 528/45; 260/239.3 R; 260/453 AL; 260/453 AR; 260/453 P; 260/553 E; 528/44; 528/51; 528/54; 528/55; 528/56; 528/58; 528/59; 528/68; 528/367; 528/423
[58] Field of Search .................. 528/423, 367, 45, 68, 528/59; 260/453 AL, 453 AR

[56] References Cited

U.S. PATENT DOCUMENTS

| | | | |
|---|---|---|---|
| 2,268,586 | 1/1942 | Gilman | 528/44 |
| 2,801,230 | 7/1957 | Fraser et al. | 528/44 |
| 3,528,949 | 9/1970 | Rutledge | 528/367 |
| 3,530,095 | 9/1970 | Ponet | 528/367 |
| 3,563,957 | 2/1971 | Beebe | 528/423 |
| 3,943,158 | 3/1976 | Dietrich et al. | 260/453 AL |
| 4,057,535 | 11/1977 | Lipatova et al. | 528/66 |

*Primary Examiner*—H. S. Cockeram
*Attorney, Agent, or Firm*—James S. Rose; Denis A. Firth

[57] ABSTRACT

Novel bis cyclic ureas are disclosed having the formula

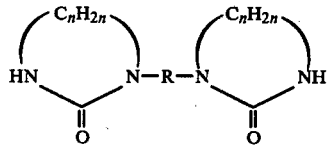

wherein $C_nH_{2n}$ represents alkylene from 4 to 12 inclusive and provided there are at least 4 carbon atoms in succession in the chain and R is the residue obtained by the removal of both halogen atoms from a diacid halide.

The bis cyclic ureas are easily converted to a novel class of aliphatic diisocyanates simply by heating. Alternatively, they are blended with polymeric polyols to form one-component storage stable compositions which are thermally converted to polyurethane resins without any significant volatile or side product formation.

4 Claims, No Drawings

POLYURETHANE FORMING COMPOSITIONS

CROSS-REFERENCE TO RELATED APPLICATION

This application is a division of copending application Ser. No. 874,402 filed Feb. 1, 1978, and now U.S. Pat. No. 4,138,398, which in turn is a continuation-in-part of copending application Ser. No. 754,189, filed Dec. 27, 1976, now abandoned.

BACKGROUND OF THE INVENTION

1. Field of the Invention

This invention relates to the preparation of cyclic ureas, and, more particularly, is concerned with the preparation of bis cyclic ureas which can act as masked diisocyanates, the diisocyanates produced thereby, and the stable one-component polyurethane forming systems containing said bis cyclic ureas.

2. Description of the Prior Art

One-can, or the commonly named one-component, polyurethane forming systems are well known, particularly, in the coating art; see for example, Saunders & Frisch, Polyurethanes: Chemistry and Technology, Parts I (pp. 8 and 118-121) and II, (pp. 453-454), 1963 and 1964 respectively, Interscience Publishers, John Wiley and Sons, New York, N.Y., and further references cited therein. The one-component systems call for the use of a "blocked" or "disguised" isocyanate with a polyol. Upon heating the one-component system, the isocyanate groups are released to react with the polyol to form the polyurethane. Unless, and until, the systems are heated they remain shelf stable and avoid the need to store and mix a number of separate components.

However, the blocked isocyanates suffer from the severe disadvantage that when the blocking agent is released during the curing phase, it is liberated into the resin where it may remain and have a deleterious effect, or, alternatively, be vaporized off where it must either be collected or released to the atmosphere. Since the commonest blocking agent is phenol this gives rise to both safety and environmental problems, not to mention the economic ones.

We have now found a novel class of bis cyclic ureas which are particularly useful in stable one-component polyurethane systems where they function as masked isocyanates. When the system is heated the bis ureas dissociate to form only the diisocyanate thereby eliminating the prior art problem of a released blocking agent.

Furthermore, the compounds prepared from the bis cyclic ureas are, themselves, a novel class of amide containing diisocyanates which are useful monomers in applications other than one-component polyurethane systems and are very simply prepared from said ureas.

SUMMARY OF THE INVENTION

This invention comprises bis cyclic ureas having the formula

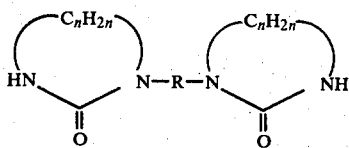
(I)

wherein $C_nH_{2n}$ represents alkylene from 4 to 12, inclusive, provided there are at least 4 carbon atoms in succession in the chain and R is a divalent radical selected from the group consisting of

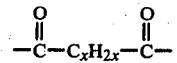

wherein $C_xH_{2x}$ represents alkylene from 1 to 8 inclusive, and

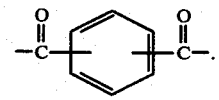

The invention also comprises a process for the preparation of the novel bis cyclic ureas (I).

The invention also comprises a process for converting a bis cyclic urea (I) into a diisocyanate having the formula

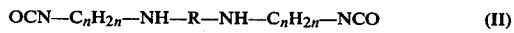
(II)

wherein $C_nH_{2n}$ and R are as defined above.

The invention also comprises the diisocyanates having the formula (II) set forth above.

The invention also comprises a storage stable composition, capable of forming a polyurethane resin upon heating said composition to a temperature in the range of about 100° C. to about 250° C., said composition comprising a mixture of a bis cyclic urea (I) and a polymeric polyol.

The invention also comprises a polyurethane resin prepared by reacting a bis cyclic urea (I) with a polymeric polyol.

The diradical —$C_nH_{2n}$— means an alkylene radical having from 4 to 12 carbon atoms, inclusive, such as butylene (tetramethylene), pentylene (pentamethylene), hexylene (hexamethylene), heptylene (heptamethylene), octylene (octamethylene), nonylene (nonamethylene), decylene (decamethylene), undecylene (undecamethylene), dodecylene (dodecamethylene), and isomeric forms thereof provided there are at least 4 carbon atoms in succession in the chain separating the valencies The diradical —$C_xH_{2x}$— means an alkylene radical having from 1 to 8 carbon atoms, inclusive, such as methylene, ethylene, propylene, butylene, pentylene, hexylene, heptylene, octylene, and isomeric forms thereof.

The term "storage stable composition" means a composition capable of standing for an indefinite period of time at a temperature of about 20° C.-30° C. without undergoing a chemical change.

The term "polymeric polyol" means any organic polyol having an average hydroxyl equivalent weight of from about 30 to about 1,500 and having from about 2 to about 8 hydroxyl groups per molecule.

The term "polymeric diol" means a polymeric polyol defined above and having 2 hydroxyl groups.

The term "difunctional extender" means a difunctional active hydrogen containing compound inclusive of glycols, diamines, amino-alcohols, and the like.

DETAILED DESCRIPTION OF THE INVENTION

The novel bis cyclic ureas of the present invention having the formula (I) set forth above are easily prepared in a novel process using the Schotten-Baumann reaction conditions for the acylation of amines or ureas; for example, see Synthetic Organic Chemistry by R. B. Wagner and H. D. Zook, p. 647, 1953, John Wiley and Sons, New York, N.Y. Typically, the appropriate cyclic urea (III) and diacid halide (IV) are reacted in an inert organic solvent at a molar ratio of 2:1 respectively and in the presence of a 2 molar proportion of an acid acceptor base compound to remove the 2 moles of HX formed from the reaction in accordance with the following equation

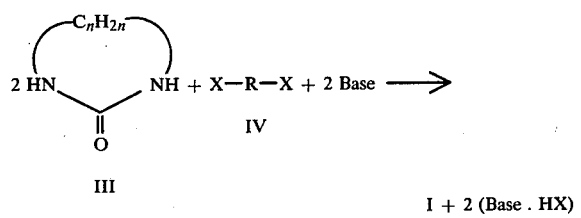

wherein the diradicals —$C_nH_{2n}$— and —R— are as defined above and X is a halogen selected from the group consisting of fluorine, chlorine, bromine, and iodine.

A preferred class of novel bis cyclic ureas (Ia) in accordance with the present invention is that prepared from the cyclic urea (IIIa) and a diacid halide (IVa) in accordance with the following equation

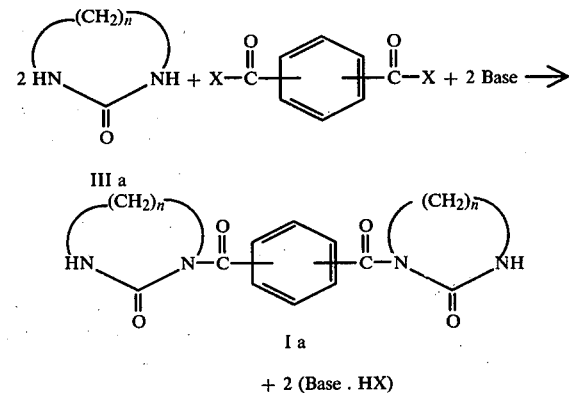

wherein n is an integer from 4 to 6 inclusive.

The preparative conditions involve procedures well known to those skilled in the art and are not critical to the present invention and optimum conditions can be easily determined by trial and error. The reaction temperature can range from about 20° C. to about 100° C. and preferably is from about 20° C. to about 80° C. The reaction time is advantageously from about 10 minutes to about 8 hours.

Typical solvents for the reaction include ethylene dichloride, chlorobenzene, ortho-dichlorobenzene, methylethyl ketone, acetonitrile, diethyleneglycol dimethyl ether, ethyleneglycol dimethyl ether, and the like.

Any base capable of removing hydrohalic acids from the reaction may be used and includes either an inorganic or organic base although the latter is generally preferred. Typical inorganic bases which can be employed are sodium hydroxide, potassium hydroxide, calcium oxide, and the like. Typical organic bases include tertiary amines such as pyridine, triethylamine, tributylamine, and the like. Generally speaking, when the tertiary amines are employed they form insoluble amine hydrohalide salts which are easily removed by filtration whereas an inorganic base such as sodium hydroxide results in the formation of the sodium halide salt and water which are both easily separated from the bis cyclic urea using liquid extraction procedures well known to those skilled in the art.

The bis cyclic ureas are readily obtained from the reaction mixture using standard product isolation techniques known to those skilled in the art. Generally speaking, after the hydrohalide salt is removed from the reaction mixture by filtration, the solution is concentrated by removing the solvent, preferably in vacuo, and the residue is triturated or recrystallized from water or other suitable solvent to yield crystalline (I).

The cyclic ureas (III) employed in the preparation of the bis cyclic ureas in accordance with the present invention are known compounds which are readily obtained using standard methods known in the art.

A preferred cyclic urea employed in the present invention has the formula (IIIa) set forth above.

Illustratively, the cyclic ureas (III) are easily obtained by the method of Ozaki et al, (J.A.C.S. 79, 4358–4360, 1957) starting with the appropriate diisocyanate (V) which is converted to the cyclic urea (III) by reaction with water.

$$OCN—C_nH_{2n}—NCO+H_2O\rightarrow III+CO_2 \qquad V$$

Illustrative examples of the cyclic ureas (III) used in the present invention include tetramethylene urea, pentamethylene urea, hexamethylene urea, heptamethylene urea, octamethylene urea, nonamethylene urea, decamethylene urea, undecamethylene urea, dodecamethylene urea, 5,5-dimethyltetramethylene urea, 5,6-dimethyltetramethylene urea, 5,5-dimethyl heptamethylene urea, and the like.

A preferred group of cyclic ureas includes tetramethylene urea, pentamethylene urea, and hexamethylene urea.

The diacid halides (IV) employed in the practice of the present invention are defined as above and a preferred diacid halide has the formula

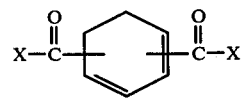

wherein X is defined hereinabove.

Exemplary of the diacid halides that can be used in the present invention are succinoyl dichloride, glutaroyl dichloride, adipoyl dichloride, pimeloyl dichloride, suberoyl dichloride, azelaoyl dichloride, sebacoyl dichloride, adipoyl dibromide, azelaoyl dibromide, sebacoyl dibromide, terephthaloyl dichloride, isophthaloyl dichloride, and phthaloyl dichloride.

A preferred group of diacid halides comprises adipoyl dichloride, azelaoyl dichloride, sebacoyl dichloride, terephthaloyl dichloride, isophthaloyl dichloride, and phthaloyl dichloride.

A particularly preferred group consists of terephthaloyl dichloride, isophthaloyl dichloride, and phthaloyl dichloride.

Although the bis cyclic ureas (I) in accordance with the present invention find particular utility as masked diisocyanates in one-component polyurethane systems which will be discussed in detail hereinafter, they also serve as a convenient source for a class of novel diisocyanates having the formula (II) set forth above.

The diisocyanate (II) is obtained simply by heating the bis cyclic urea at a temperature high enough to cause its dissociation. The heating may be carried out in the absence of solvent, however, the bis cyclic ureas (I) in their most purified form are crystalline compounds and it is generally preferable to carry out the conversion in a solvent in the absence of moisture. The resulting solution of the diisocyanate (II) can then be employed in some further operation in the form of a solution, or, optionally, the solvent may be removed using standard methods known to those skilled in the art, for example, distillation, vacuum concentration, thin-film evaporation, etc., to provide the pure diisocyanate.

The conversion is advantageously carried out within a temperature range of about 100° C. to about 250° C., preferably from about 150° C. to about 180° C. for a period of time from about 5 minutes to about 5 hours and preferably from about 10 minutes to about 30 minutes.

Solvent choice is not critical and any solvent which is inert to both the bis urea (I) and diisocyanate (II) may be used in the dissociation reaction provided its boiling point is high enough to permit heating of the solution to affect the dissociation of I to II. Typical solvents include those used in the preparation of the bis cyclic ureas (I) set forth above. Advantageously, the same solvent in which the urea (I) is prepared is used for the dissociation reaction.

A preferred class of diisocyanates are those having the formula

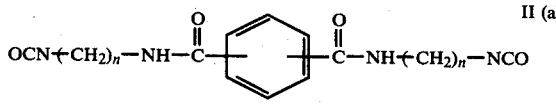

II (a)

These diisocyanates are obtained from the dissociation of the bis cyclic ureas having the formula (Ia) set forth above.

The diisocyanates (II) embrace a novel class which includes (a) aliphatic amide containing aliphatic diisocyanates, and (b) aromatic amide containing aliphatic diisocyanates. These diisocyanates can be converted to a variety of condensation polymers using procedures well known in the art. Illustratively, they can be converted to non-cellular polyurethanes for use in elastomers, coatings, fibers, and adhesives, using procedures such as those described in Saunders et al., Polyurethanes, Chemistry and Technology, Part II, Interscience Publishers, New York, 1964. The polyurethanes so prepared are characterized by greater color stability on exposure to sunlight or ultraviolet irradiation compared with corresponding polyurethanes prepared from aromatic diisocyanates.

The bis cyclic ureas (I) find particular utility as masked diisocyanates in one-component or one-can polyurethane systems. The bis cyclic urea (I) is thoroughly blended with a polymeric polyol in essentially stoichiometric proportions at a temperature below 65° C., preferably from about 20° C. to about 65° C., using any suitable mixing procedure known to those skilled in the art, and preferably under anhydrous conditions to exclude moisture.

The resulting blend is a storage stable composition which can be stored for an indefinite period of time at a reasonable ambient temperature, for example 20°–30° C., without undergoing reaction to form polyurethane.

Upon heating said storage stable composition to a temperature in the range of about 100° C. to about 250° C., the bis cyclic urea (I) and polymeric polyol undergo reaction to form a polyurethane resin. Heating time should be sufficient to complete the reaction between the polyol and masked isocyanate and will vary according to the viscosity of the blend composition, the chemical structure of the polyol, and the presence or absence of a polyurethane catalyst, and, most importantly, temperature. Optimum conditions of time and temperature for any given system are easily determined by trial and error on small aliquot samples of the composition.

It is frequently desirable, but not essential, to include a catalyst in the reaction mixture employed to prepare the compositions of the invention. Any of the catalysts conventionally employed in the art to catalyze the reaction of an isocyanate with a reactive hydrogen containing compound can be employed for this purpose; see for example, Saunders et al., Polyurethanes, Chemistry and Technology, Part I, Interscience, New York, 1963, pages 228–232; see also Britain et al., J. Applied Polymer Science, 4, 207–211, 1960. Such catalysts include organic and inorganic acid salts of, and organometallic derivatives of, bismuth, lead, tin, iron, antimony, uranium, cadmium, cobalt, thorium, aluminum, mercury, zinc, nickel, cerium, molybdenum, vanadium, copper, manganese and zirconium, as well as phosphines and tertiary organic amines. Representative organotin catalysts are stannous octoate, stannous oleate, dibutyltin dioctoate, dibutyltin dilaurate, and the like. Representative tertiary organic amine catalysts are triethylamine, triethylenediamine, N,N,N',N'-tetramethylethylenediamine, N,N,N',N'-tetraethylethylenediamine, N,methylmorpholine, N-ethylmorpholine, N,N,N',N'-tetramethylguanidine, N,N,N',N'-tetramethyl-1,3-butanediamine, N,N-dimethylethanolamine, N,N-diethylethanolamine, and the like. The amount of catalyst employed is generally within the range of about 0.02 to about 2.0 percent by weight based on the total weight of the reactants.

The polymeric polyols employed in the storage stable composition and defined hereinabove include any of the polyols set forth in U.S. Pat. Nos. 3,745,133 and 3,423,344 the disclosures of which are incorporated herein by reference.

It will be understood by those skilled in the art that when the polymeric polyol employed in the storage stable compositions of the invention has more than two hydroxy groups, the resulting polyurethane resin will be highly cross-linked and give rise to a solid, hard, and high modulus polyurethane resin in the absence of modifying agents. Polyurethanes produced thereby can be used particularly for potting and encapsulating electrical components.

In a preferred embodiment of the storage stable compositions in accordance with the present invention the bis cyclic ureas (Ia) are blended with a mixture of a polymeric diol as defined above, and a difunctional extender, and a polyurethane catalyst. Upon heating, this composition is converted to an elastomeric polyurethane resin. The proportions of urea and diol extender combination are chosen so that the ratio of the equivalents of isocyanate arising from the urea dissociation to the total number of hydroxyl or active hydrogen groups in the polymeric diol and extender is within the range of 0.95:1 to 1.10:1 and preferably within the range of 0.98:1 to 1.04:1. Further, as will be appreciated by one skilled in the art, the proportion of polymeric diol to extender can be varied within a wide range depending largely upon the desired hardness of the final polyurethane elastomer. Advantageously, the molar proportion of polymeric diol to extender is within the range of 0.05:1 to 2:1 and, preferably, within the range of 0.1:1 to 1:1.

If desired, the elastomers of the invention can have incorporated in them, at any appropriate stage of preparation, additives such as pigments, fillers, lubricants, stabilizers, antioxidants, coloring agents, fire retardants, and the like, which are commonly used in conjunction with polyurethane elastomers.

Exemplary of the polymeric diols which can be employed in the storage stable compositions of the invention are hydroxyl terminated polyesters or polyethers. Illustrative of the polyether polyols are polyoxyalkylene glycols such as polytetramethylene glycol, the polyoxyethylene glycols prepared by the addition of ethylene oxide to water, ethylene glycol or diethylene glycol; polyoxypropylene glycols prepared ty the addition of 1,2-propylene oxide to water, propylene glycol or dipropylene glycol; mixed oxyethylene oxypropylene glycols prepared in a similar manner utilizing a mixture of ethylene oxide or propylene oxide or a sequential addition of ethylene oxide and 1,2-propylene oxide; polyether glycols prepared by reacting ethylene oxide, propylene oxide, or mixtures thereof with mono- and polynuclear dihydroxybenzene, e.g. catechol, resorcinol, hydroquinone, orcinol, 2,2-bis(p-hydroxyphenyl)propane, bis(p-hydroxyphenyl)methane and the like.

Illustrative of polyester polyols are those prepared by polymerizing ε-caprolactone using an initiator such as ethylene glycol, ethanolamine and the like, and those prepared by esterification of polycarboxylic acids such as phthalic, terephthalic, succinic, glutaric, adipic acids and the like with polyhydric alcohols such as ethylene glycol, butanediol, and the like.

The difunctional extenders which can be employed in preparing the storage stable compositions of the invention can be any of the difunctional active hydrogen containing extenders commonly employed in the art. The latter are inclusive of glycols, diamines, amino alcohols, and the like. Illustrative of diol extenders are aliphatic diols, advantageously containing from 2 to 6 carbon atoms, inclusive, such as ethylene glycol, 1,3-propylene glycol, 1,2-propylene glycol, 1,4-butanediol, 1,2-hexanediol, neopentyl glycol, and the like; and dihydroxyalkylated aromatic compounds such as the bis(2-hydroxyethyl)ethers of hydroquinone and resorcinol; p-xylene-α,α'-diol; the bis(2-hydroxyethyl)ether of p-xylene-α,α'-diol; m-xylene-α,α'-diol and the bis(2-hydroxyethyl)ether thereof. Illustrative of diamine extenders are aromatic diamines such as p-phenylenediamine, m-phenylenediamine, benzidine, 4,4'-methylenedianiline, 4,4'-methylenebis(2-chloroaniline) and the like. Illustrative of amino alcohols are ethanolamine, propanolamine, butanolamine, and the like.

The storage stable compositions can be used in the preparation of (i) polyurethane coatings, particularly wire coating; (ii) coatings for metals because of their high adhesion properties to metals and other surfaces due to free isocyanate generation upon heating; and (iii) sealants, gaskets, seals, and the like. Furthermore, these applications of the compositions of the invention can be conducted at elevated temperatures and do not give rise to any volatile by-product formation.

The following examples describe the manner and process of making and using the invention and set forth the best mode contemplated by the inventors of carrying out the invention but are not to be construed as limiting.

EXAMPLE 1

A 250 ml. reaction flask equipped with a mechanical stirrer, a reflux condenser, thermometer, and addition funnel was charged with 6.84 g. (0.06 mole) of tetramethylene urea, 10.1 g. (0.1 mole) of triethylamine, and 150 ml. of ethylene dichloride. The mixture was stirred to form a solution and, at room temperature (about 25° C.) and over a period of about 22 minutes, a solution of 6.09 g. (0.03 mole) of isophthaloyl chloride, dissolved in 30 ml of ethylene dichloride, was added during constant stirring. Reaction temperature during the addition slowly rose to 42° C. and the solution became cloudy as a precipitate formed.

The reaction mixture was cooled and filtered to collect 5.95 g. of the hydrochloride salt of triethylamine. Evaporation of the filtrate provided 20.05 g. of thick liquid residue. It was triturated in excess ethyl acetate until it was crystalline then filtered. A crystalline solid was obtained, wt.=6.75 g., m.p.=185°-200° C. The crystalline solid was triturated in 100 ml. of water, filtered, washed with fresh water, and dried to yield 3 g. of crystalline N,N'-isophthaloyl bis(tetramethylene urea) which melted at 225°-230° C. This compound is a bis cyclic urea in accordance with the present invention and corresponds to the following formula

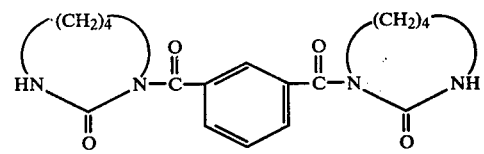

Using the procedure and ingredients set forth above except that either the isophthaloyl chloride is replaced by the equivalent amount of the following diacid chlorides, or else the tetramethylene urea is replaced by the equivalent amount of the following cyclic ureas, there are produced the corresponding bistetramethylene ureas and N,N'-isophthaloyl bis cyclic ureas in accordance with the present invention.

| Diacid chloride | Bistetramethylene urea |
|---|---|
| Terephthaloyl chloride | N,N'-Terephthaloyl bis(tetramethylene urea) |
| Adipoyl chloride | N,N'-Adipoyl bis(tetramethylene urea) |
| Azelaoyl chloride | N,N'-Azelaoyl bis(tetramethylene urea) |
| Sebacoyl chloride | N,N'-Sebacoyl bis(tetramethylene urea) |
| α-Methyladipoyl chloride | N,N'-(α-Methyladipoyl)bis(tetramethylene urea) |
| Cyclic Urea | Bis Cyclic Urea |
| Pentamethylene urea | N,N'-Isophthaloyl bis(penta- |

| | -continued |
|---|---|
| | methylene urea) |
| Hexamethylene urea | N,N'-Isophthaloyl bis(hexamethylene urea) |
| Octamethylene urea | N,N'-Isophthaloyl bis(octamethylene urea) |
| 5,5-Dimethyltetramethylene urea | N,N'-Isophthaloyl bis(5,5-dimethyltetramethylene urea) |
| 5,6-Dimethyltetramethylene urea | N,N'-Isophthaloyl bis(5,6-dimethyltetramethylene urea) |

Stability of N,N'-Isophthaloyl Bis(Tetramethylene Urea)

A 0.5 g. sample of N,N'-isophthaloyl bis(tetramethylene urea) and 25 ml. of methanol were heated for 5 hours under reflux (temperature range of 64° C.–67° C.). The mixture was cooled then filtered to obtain 0.3 g. of the starting compound, m.p.=235°-240° C. The remainder of the starting bis urea was soluble in the methanol. The N,N'-isophthaloyl bis(tetramethylene urea) was therefore characterized as stable at 65° C. since no carbamate formed upon heating in the methanol.

Dissociation of N,N'-Isophthaloyl Bis(Tetramethylene Urea) to N,N'-Di(4-Isocyanatobutyl)Isophthalamide A 0.25 g. sample of N,N'-isophthaloyl bis(tetramethylene urea) and 10 ml. of ortho dichlorobenzene (ODCB) were placed in a 25 ml. round bottom flask equipped with a reflux condenser, stirrer and thermometer. The mixture was heated during stirring and when the solution started to reflux (at 180° C.), samples of the solution were removed and analyzed by infrared absorption spectroscopy. Isocyanate absorption at 4.34μ was evident in the first sample taken and dissociation of the diurea was complete within 30 minutes at 180° C. Thus there was obtained N,N'-di(4-isocyanatobutyl)isophthalamide in accordance with the present invention and corresponding to the formula

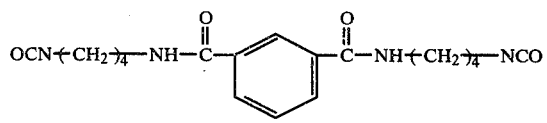

It was characterized by infrared absorption analysis including the characteristic isocyanate absorption at 4.34μ.

Using the above procedure of heating in ODCB at 180° C. the bistetramethylene ureas and bis cyclic ureas set forth below there are produced the corresponding diisocyanates in accordance with the present invention set forth below.

| Bis Urea | Diisocyanate |
|---|---|
| N,N'-Terephthaloyl bis(tetramethylene urea) | N,N'-Di)4-isocyanatobutyl)terephthalamide |
| N,N'-Adipoyl bis(tetramethylene urea) | N,N'-Di(4-isocyanatobutyl)adipamide |
| N,N'-Azelaoyl bis(tetramethylene urea) | N,N'-Di(4-isocyanatobutyl)azelamide |
| N,N'-Sebacoyl bis(tetramethylene urea) | N,N'-Di(4-isocyantobutyl)sebacamide |
| N,N'-(αMethyladipoyl)bis(tetramethylene urea) | N,N'-Di(4-isocyanatobutyl)α-methyladipamide |
| N,N'-Isophthaloyl bis(pentamethylene urea) | N,N'-Di(5-isocyanatopentyl)isophthalamide |
| N,N'-Isophthaloyl bis(hexamethylene urea) | N,N'-Di(6-isocyanatohexyl)isophthalamide |
| N,N'-Isophthaloyl bis(octamethylene urea) | N,N'-Di(8-isocyanatooctyl)isophthalamide |
| N,N'-Isophthaloyl bis(5,5-dimethyltetramethylene urea) | N,N'-Di(4-isocyanato-2,2-dimethylbutyl)isophthalamide |
| N,N'-Isophthaloyl bis(5,6-dimethyltetramethylene urea | N,N'-Di(4-isocyanato-2,3-dimethylbutyl)isophthalamide |

EXAMPLE 2

A 1.79 g. (0.005 mole) sample of N,N'-isophthaloyl bis-(tetramethylene urea) and 3.31 g. (0.005 mole) of Teracol 650 (a tetramethyleneglycol, E.W.=331, supplied by E. I. DuPont Company, Wilmington, Del.) were mixed in a test tube and degassed at 100° C. under vacuum of about 0.1 mm. The reactants were not completely miscible at this temperature.

The temperature was slowly raised and at 210°–215° C. a clear homogeneous solution had formed. Heating was continued at about 220°–230° C. for 15 minutes then the hot clear solution was poured into an aluminum dish. Upon cooling, it formed a hard resilient dark yellow polymer characterized by the following recurring unit

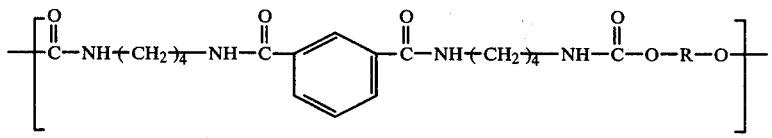

wherein R corresponds to the divalent residue formed by the removal of the two hydroxyl groups of Teracol 650.

We claim:
1. A polyurethane resin prepared by heating a bis cyclic urea having the formula

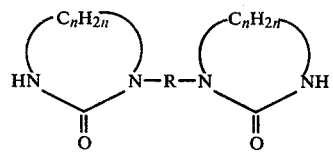

wherein $C_nH_{2n}$ is alkylene from 4 to 12 inclusive and provided there are at least 4 carbon atoms in succession in the chain and R is a divalent radical selected from the group consisting of

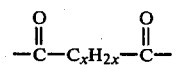

wherein $C_xH_{2x}$ is alkylene from 1 to 8 inclusive, and

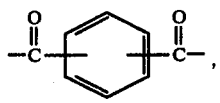, with a polymeric polyol at a temperature sufficiently high to cause dissociation of said urea.

2. A storage stable composition capable of forming a polyurethane resin upon heating said composition to a temperature in the range of about 100° C. to about 250° C. which composition comprises a mixture of:

(a) a bis cyclic urea having the formula

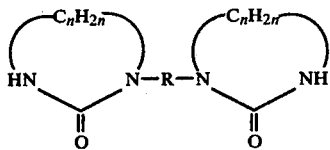

wherein $C_nH_{2n}$ is alkylene from 4 to 12 inclusive and provided there are at least 4 carbon atoms in succession in the chain and R is a divalent radical selected from the group consisting of

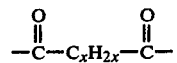

wherein $C_xH_{2x}$ is alkylene from 1 to 8 inclusive, and

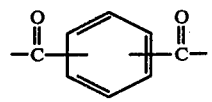

and (b) a polymeric polyol.

3. A storage stable composition according to claim 2 containing a polyurethane catalyst.

4. A storage stable composition capable of forming a polyurethane resin upon heating said composition to a temperature in the range of about 100° C. to about 250° C. which composition comprises a mixture of:

(a) a bis cyclic urea having the formula

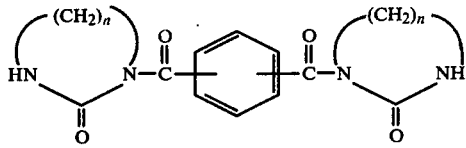

wherein n is an integer from 4 to 6 inclusive;
(b) a polymeric diol;
(c) a difunctional extender; and
(d) a polyurethane catalyst.

* * * * *

UNITED STATES PATENT OFFICE
CERTIFICATE OF CORRECTION

Patent No. 4,217,436  Dated August 12, 1980

Inventor(s) Reinhard H. Richter, Benjamin W. Tucker and Henri Ulrich

It is certified that error appears in the above-identified patent and that said Letters Patent are hereby corrected as shown below:

Abstract of the Disclosure (2nd printed line), "$C_nH_{an}$" should read --$C_nH_{2n}$--; column 3, line 40, missing under right-hand side of formula --IVa--; Column 4, lines 52-55, that portion of formula which reads

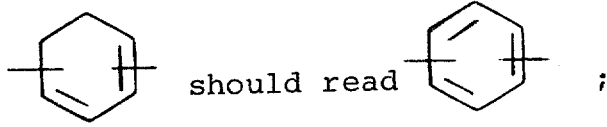 should read 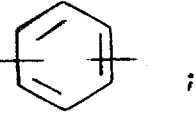 ;

Column 10, line 6, "N,N'-(αMethyladipoyl)" should read --N,N'-(α-Methyladipoyl)--.

Signed and Sealed this

Twenty-fourth Day of February 1981

[SEAL]

Attest:

RENE D. TEGTMEYER

Attesting Officer   Acting Commissioner of Patents and Trademarks